United States Patent
Saegusa

(10) Patent No.: US 8,689,615 B2
(45) Date of Patent: Apr. 8, 2014

(54) BUBBLE PRESENCE/ABSENCE DETERMINING METHOD AND DISPENSING APPARATUS

(75) Inventor: Isao Saegusa, Shizouka (JP)

(73) Assignee: Beckman Coulter, Inc., Brea, CA (US)

(*) Notice: Subject to any disclaimer, the term of this patent is extended or adjusted under 35 U.S.C. 154(b) by 837 days.

(21) Appl. No.: 12/875,848

(22) Filed: Sep. 3, 2010

(65) Prior Publication Data
US 2010/0327012 A1  Dec. 30, 2010

Related U.S. Application Data

(63) Continuation of application No. PCT/JP2009/053528, filed on Feb. 26, 2009.

(30) Foreign Application Priority Data

Mar. 7, 2008  (JP) .................. 2008-058232

(51) Int. Cl.
*G01N 35/10*  (2006.01)
(52) U.S. Cl.
USPC .......... 73/61.78; 422/107; 422/501; 422/509; 422/521

(58) Field of Classification Search
CPC ......... G01N 35/1009; G01N 35/1016; G01N 35/1097; G01N 2035/1018
USPC ......... 73/61.78; 422/105–107, 500, 501, 509, 422/521; 436/180
See application file for complete search history.

(56) References Cited

U.S. PATENT DOCUMENTS

| 5,723,795 A | 3/1998 | Merriam | |
|---|---|---|---|
| 7,792,647 B1 * | 9/2010 | Ding et al. | 702/35 |
| 2008/0289437 A1 | 11/2008 | Saegusa | |

FOREIGN PATENT DOCUMENTS

| JP | 06-027120 A | | 2/1994 |
|---|---|---|---|
| JP | 10-227799 A | | 8/1998 |
| JP | 11-501399 A | | 2/1999 |
| JP | 2003-254982 A | | 9/2003 |
| JP | 2007-47083 | * | 2/2007 |
| JP | 2007-315872 | * | 12/2007 |
| WO | WO 2007/119662 A1 | | 10/2007 |

* cited by examiner

*Primary Examiner* — Daniel S Larkin
(74) *Attorney, Agent, or Firm* — Kilpatrick Townsend & Stockton LLP

(57) ABSTRACT

The present invention relates to a method for determining the presence or absence of bubbles inside pipes in a dispensing apparatus and a dispensing apparatus.

4 Claims, 6 Drawing Sheets

BUBBLE PRESENCE/ABSENCE DETERMINING METHOD AND DISPENSING APPARATUS

CROSS-REFERENCE TO RELATED APPLICATIONS

This application is a continuation of International Application No. PCT/JP2009/053528, filed Feb. 26, 2009, which claims benefit of priority to Japanese Application No. 2008-058232, filed Mar. 7, 2008, the disclosures of each are herein incorporated by reference.

TECHNICAL FIELD

The present invention relates to a bubble presence/absence determining method for determining the presence or absence of bubbles inside pipes in a dispensing apparatus, and a dispensing apparatus.

BACKGROUND ART

Conventionally, a dispensing apparatus used in dispensing a liquid sample containing a specimen or a reagent in an analyzing apparatus dispenses a liquid sample by suctioning or draining a liquid, for example, a cleaning liquid, in the pipes with a feeding/draining pump so as to suction the liquid sample through a dispensing nozzle connected to the pipes, and discharging the suctioned liquid sample to a predetermined position. In such a case, if bubbles mix in the cleaning liquid, the dispensing apparatus has a decreased dispensing accuracy for the liquid sample due to the bubbles. Thus, the dispensing apparatus has the pipes filled with a deaerated cleaning liquid.

However, in a case of dispensing for a long period of time, or in a case of replacing parts connected to the pipes in maintenance or the like, slight bubbles may mix in the pipes. In such a case, since it is not easy to find the bubbles, the dispensing apparatus is used with bubbles mixed in, and as a result, analysis is conducted while a dispensing operation is performed with a decreased dispensing accuracy. There has been such a problem.

Thus, in order to solve this problem, a dispensing apparatus having a function of detecting the presence of bubbles in pipes has been proposed (see Patent Document 1).

Patent Document 1: Japanese Laid-Open Publication No. 2003-254982

DISCLOSURE OF THE INVENTION

Problem to be Solved by the Invention

However, the conventional dispensing apparatus having a function of detecting the presence of bubbles in pipes has the following problem: since the conventional dispensing apparatus raises an alarm to notify one of the presence of bubbles after dispensing a specimen, it is impossible to detect the presence of bubbles beforehand, which forces one to conduct reexaminations due to the decreased dispensing accuracy, resulting in longer analysis time.

The present invention has been completed in view of the foregoing, and aims to provide a bubble presence/absence determining method and a dispensing apparatus which allows one to surely detect the presence of bubbles before dispensing.

Means for Solving the Problem

In order to solve the aforementioned problem and achieve the aforementioned purpose, the present invention is featured by a method of determining the presence or absence of bubbles inside pipes of a dispensing apparatus which dispenses by filling a liquid in pipes connected to a dispensing nozzle, moving the liquid inside the pipes to suction a liquid sample containing a specimen or a reagent through the dispensing nozzle, and discharging the suctioned liquid sample, characterized in that the method includes: a detecting step of detecting pressure inside the pipes; a calculating step of calculating a slope of each of a plurality of pressure waveform portions obtained by dividing the pressure waveform detected by the detecting step such that the plurality of pressure waveform portions correspond to a plurality of segments along the time axis; and a determining step of determining the presence or absence of bubbles inside the pipes based on the number of segments in which the respective slopes of the pressure waveform portions calculated by the calculating step are outside the ranges of slopes indicating the absence of bubbles pre-established for the respective segments.

Furthermore, the method of the present invention of determining the presence or absence of bubbles inside pipes in a dispensing apparatus is characterized in that, in the aforementioned invention, the determining step determines that bubbles are present inside the pipes when the number of the segments is one or more.

Moreover, in order to solve the aforementioned problem and achieve the aforementioned purpose, the dispensing apparatus of the present invention is a dispensing apparatus which dispenses by filling a liquid in pipes connected to a dispensing nozzle, moving the liquid inside the pipes to suction a liquid sample containing a specimen or a reagent through the dispensing nozzle, and discharging the suctioned liquid sample, characterized in that the dispensing apparatus includes: a detecting means for detecting pressure inside the pipes; a calculating means for calculating a slope of each of a plurality of pressure waveform portions obtained by dividing the detected pressure waveform such that the plurality of pressure waveform portions correspond to a plurality of segments along the time axis; and a determining means for determining the presence or absence of bubbles inside the pipes based on the number of segments in which the respective slopes of the pressure waveform portions calculated by the calculating means are outside the ranges of slopes indicating the absence of bubbles pre-established for the respective segments.

Furthermore, the dispensing apparatus of the present invention is characterized in that, in the aforementioned invention, the determining means determines that bubbles are present inside the pipes when the number of the segments is one or more.

Effect of the Invention

According to the present invention, after detecting pressure inside the pipes and calculating a slope of each of a plurality of pressure waveform portions obtained by dividing the detected pressure waveform such that the plurality of pressure waveform portions correspond to a plurality of segments along the time axis, the presence or absence of bubbles inside the pipes is determined based on the number of segments in which the respective calculated slopes of the waveform portions are out of the ranges of slopes indicating the absence of bubbles pre-established for the respective segments. Thus, the present invention attains an effect where the presence of bubbles can be surely detected before dispensing.

Figure 1:
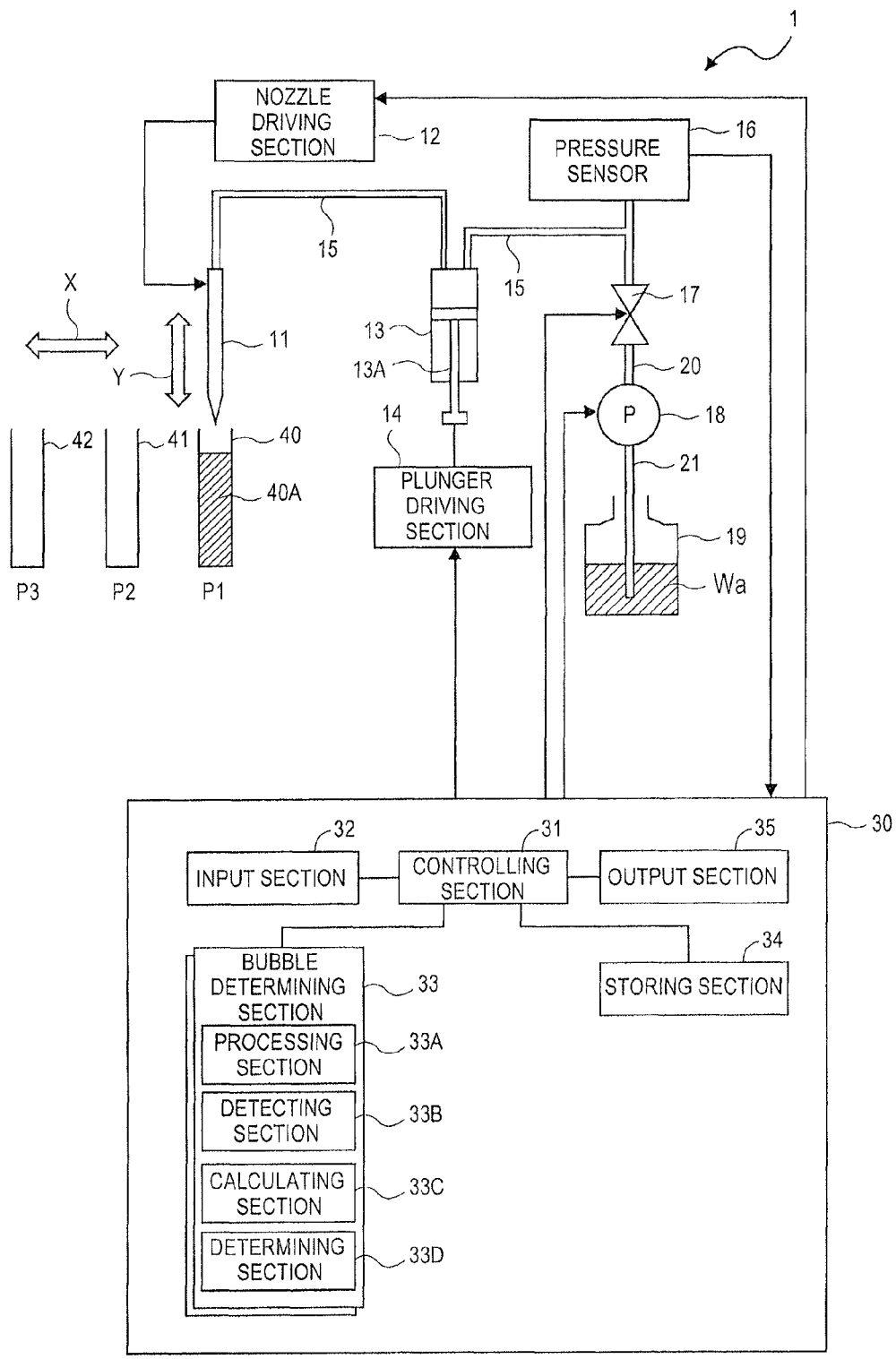
FIG. 1 is a block diagram illustrating a structure of a dispensing apparatus of an embodiment of the present invention.

EXPLANATION OF SYMBOLS 1 dispensing apparatus
11 dispensing nozzle
12 nozzle driving section
13 dispensing pump
13a plunger
14 plunger driving section
15, 20, 21 pipe
16 pressure sensor
17 electromagnetic valve
18 cleaning liquid pump
19 cleaning liquid tank
30 controlling mechanism
31 controlling section
32 input section
33 bubble determining section
33a processing section
33b detecting section
33c calculating section
33d determining section
34 storing section
35 output section
40 specimen container
41 reaction container
42 cleaning container
Wa cleaning liquid

BEST MODE FOR CARRYING OUT THE INVENTION

Hereinafter, a preferred embodiment of a method of determining the presence or absence of bubbles inside pipes in a dispensing apparatus and a dispensing apparatus of the present invention will be described with reference to the drawings. It should be noted that the invention is not limited by such an embodiment. It should also be noted that corresponding parts of the figures are given the same reference numerals in the description of the drawings.

FIG. 1 is a block diagram illustrating a structure of a dispensing apparatus of an embodiment of the present invention. This dispensing apparatus 1 is, for example, a dispensing apparatus which dispenses by suctioning a liquid sample containing a specimen or a reagent and discharging the suctioned liquid sample. As shown in FIG. 1, the dispensing apparatus 1 includes a dispensing nozzle 11, a dispensing pump 13, a pressure sensor 16, a cleaning liquid pump 18 and a controlling mechanism 30.

The dispensing nozzle 11 is made of stainless steel or the like formed into a bar-tube shape, and is moved by a nozzle driving section 12 in a horizontal direction shown in the figure as an arrow X and in a vertical direction shown in the figure as an arrow Y. A specimen container 40 containing a specimen 40a, a reaction container 41 where the specimen 40a is discharged, and a cleaning container 42 where cleaning water Wa is discharged are respectively placed at positions P1, P2, and P3.

The dispensing pump 13 is embodied by a syringe pump, and is connected, via pipes 15, to the dispensing nozzle 11, a pressure sensor 16 for detecting pressure inside the pipes 15, and to an electromagnetic valve 17 for adjusting a flow of the cleaning liquid Wa. Using reciprocation of a plunger 13a by a plunger driving section 14, the dispensing pump 13 suctions specimen 40a into the dispensing nozzle 11 and discharges the suctioned specimen 40a into the reaction container 41. The plunger driving section 14 limits travel or the like of plunger 13a under the control by a controlling section 31. Meanwhile, another pipe 20 is connected to the electromagnetic valve 17, and the other end of the pipe 20 is connected to a cleaning liquid pump 18 for supplying the cleaning liquid Wa. Furthermore, another pipe 21 is connected to the cleaning liquid pump 18, and the other end of the pipe 21 reaches a cleaning liquid tank 19 containing the cleaning liquid Wa.

The pressure sensor 16 detects pressure inside the pipes 15, and outputs the detected analog pressure signal to the controlling section 31.

The cleaning liquid pump 18 suctions the cleaning liquid Wa stored in the cleaning liquid tank 19, and supplies the cleaning liquid Wa inside the pipes 15 via the electromagnetic valve 17 provided between the cleaning liquid pump 18 and the pressure sensor 16. Here, the electromagnetic valve 17 is, under the control by the controlling section 31, opened when the suctioned cleaning liquid Wa is supplied inside the pipes 15 and closed when the dispensing nozzle 11 suctions or discharges the specimen 40a via the dispensing pump 13. The cleaning liquid Wa is an incompressible fluid such as a deaerated ion exchange water or distilled water.

The controlling mechanism 30 includes the controlling section 31, an input section 32, a bubble determining section 33, a storing section 34 and an output section 35. The nozzle driving section 12, the plunger driving section 14, the pressure sensor 16, the electromagnetic valve 17, the cleaning liquid pump 18 and the aforementioned sections in the controlling mechanism 30 are connected to, and controlled by, the controlling section 31.

The controlling section 31 is configured using a CPU or the like, and controls processing and operation of each section of the dispensing apparatus 1. The controlling section 31 performs predetermined input/output control of information input to these respective components, and performs predetermined information processing on such information.

The input section 32 is embodied by using a keyboard, a mouse, a touch panel having input/output function, or the like. Instruction information or the like necessary for dispensing the specimen is input into the input section 32. The input section 32 may also be configured to obtain and transmit instruction information for the controlling section 31 via a communication network not shown.

The bubble determining section 33 has a processing section 33a, a detecting section 33b, a calculating section 33c and a determining section 33d. The processing section 33a amplifies a pressure signal output from the pressure sensor 16, and performs a conversion process to convert the amplified pressure signal into digital signal. Specifically, the processing section 33a is embodied by an A/D converter or the like. The detecting section 33b detects pressure inside the pipes 15 from the pressure signal converted into the digital signal by the processing section 33a. The calculating section 33c calculates a slope of each of a plurality of pressure waveform portions obtained by dividing the pressure waveform shown by the pressure signal detected by the detecting section 33b such that the plurality of pressure waveform portions correspond to a plurality of segments along the time axis. The determining section 33d determines the presence or absence of bubbles inside the pipes 15 based on the number of segments in which the slopes calculated by the detecting section 33b are out of the ranges of pre-established slopes indicating the absence of bubbles.

The storing section 34 is embodied by using a hard disk for magnetically storing information, and a memory for electrically storing various programs for a processing loaded from the hard disk when the dispensing apparatus 1 performs the processing. The storing section 34 may also include an auxiliary storage capable of reading information stored on a storage medium such as CD-ROM, DVD-ROM, PC card or the like. Furthermore, the storing section 34 stores the pre-established slopes indicating the absence of bubbles for the respective predetermined segments. The output section 35 is configured using a display, a printer, a speaker and the like, and outputs various information.

The dispensing apparatus 1 thus configured, under the control of the controlling section 31, suctions the cleaning liquid Wa from the cleaning liquid tank 19 using the cleaning liquid pump 18, opens the electromagnetic valve 17, and supplies and fills the cleaning liquid Wa in the pipes 15, the dispensing pump 13 and the dispensing nozzle 11. Thereafter, the controlling section 31 closes the electromagnetic valve 17, terminates the operation of the cleaning liquid pump 18, drives the plunger driving section 14, cleans inside the dispensing nozzle 11 with the cleaning liquid Wa, and discharges the cleaning liquid Wa into the cleaning container 42 placed at the position P3. Thereafter, the controlling section 31 suctions a predetermined amount of air to the top of the dispensing nozzle 11, and under the driving of the nozzle driving section 12, moves the dispensing nozzle 11 to the specimen container 40 placed at the position P1, and suctions the specimen 40a into the dispensing nozzle 11. Thereafter, the controlling section 31 slightly discharges the specimen 40a suctioned by the dispensing nozzle 11 to the specimen container 40, and under the driving of the nozzle driving section 12, moves the dispensing nozzle 11 to the reaction container 41 placed at the position P2 and discharges the specimen 40a in the dispensing nozzle 11. Thus, a series of dispensing operations to dispense one specimen 40a from the specimen container 40 to the reaction container 41 are completed. It should be noted that, in a case of suctioning or discharging the specimen 40a with the top portion of the dispensing nozzle 11, there is an air layer between the specimen 40a and the cleaning liquid Wa, and thus the specimen 40a does not mix with the cleaning liquid Wa.

Figure 2:
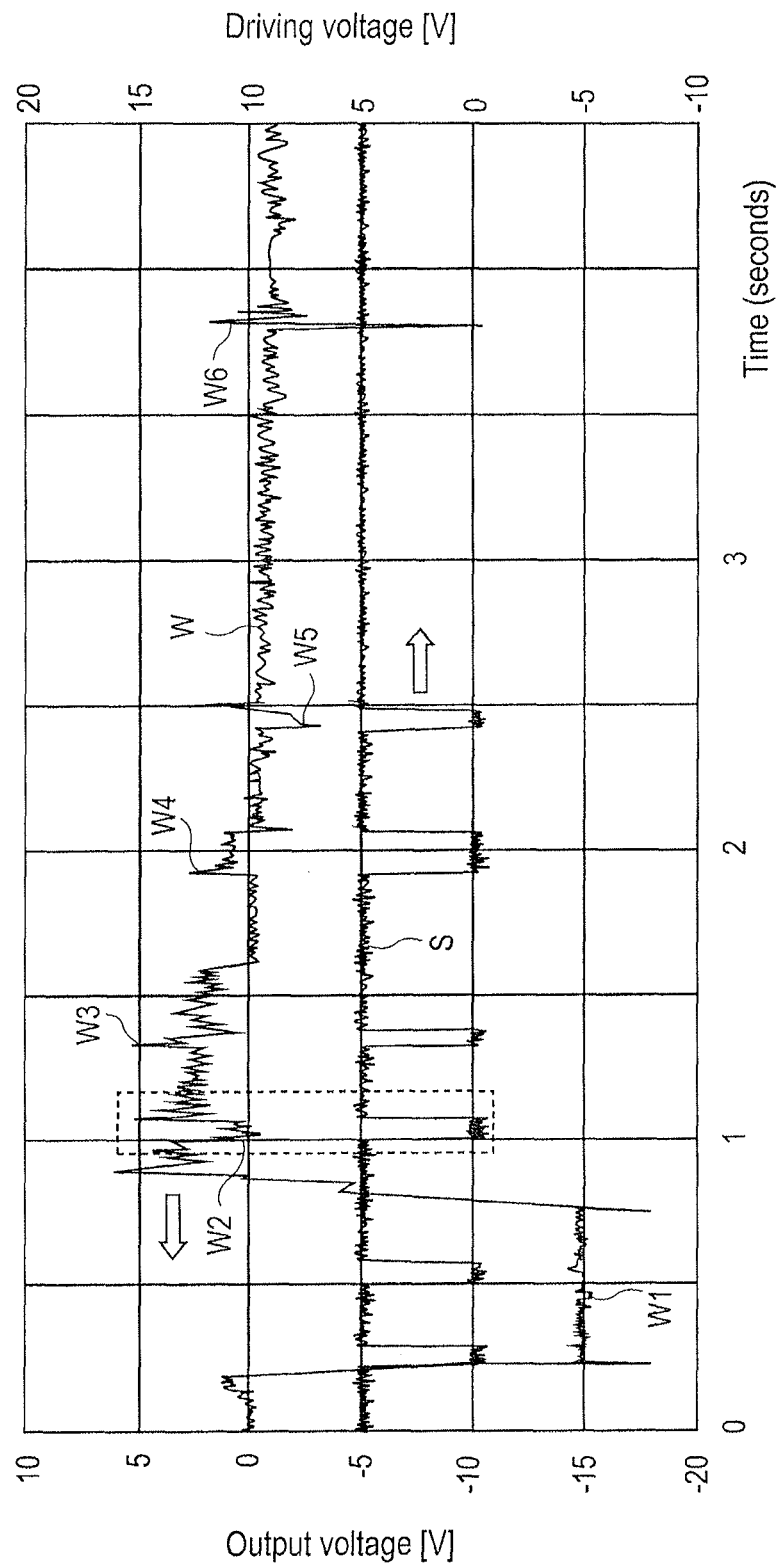
FIG. 2 is a waveform diagram illustrating a pressure waveform of a cleaning liquid inside pipes, which is detected by a pressure sensor.

Next, referring to FIG. 2, a pressure waveform in the pipes 15 detected by the pressure sensor 16 will be explained. This pressure waveform W represents a change in pressure inside the pipe 15 at the time of dispensing of the specimen by the dispensing apparatus 1 represented by an output voltage of the pressure sensor 16. In FIG. 2, a horizontal axis represents time (in seconds) and a left vertical axis represents output voltage (V) of pressure signal output by the pressure sensor 16, and a right vertical axis represents driving voltage (V) of driving signal S to drive the plunger 13a in the dispensing pump 13, which is output from the controlling section 31 to the plunger driving section 14.

As shown in FIG. 2, as pressure waveform W, the following pressure waveforms serially appear: pressure waveform W1 at the time of cleaning inside the dispensing nozzle 11; pressure waveform W2 at the time of discharging the cleaning liquid Wa; pressure waveform W3 at the time of suctioning the predetermined amount of air into the top of the dispensing nozzle 11; pressure waveform W4 at the time of suctioning the predetermined amount of specimen into the dispensing nozzle 11; pressure waveform W5 at the time of discharging excess amounts of specimen in the dispensing nozzle 11, which has been suctioned in an amount slightly more than the amount necessary for analysis, to the specimen container 40; and pressure waveform W6 at the time of discharging the suctioned specimen inside the dispensing nozzle 11 to the reaction container 41.

Figure 3:
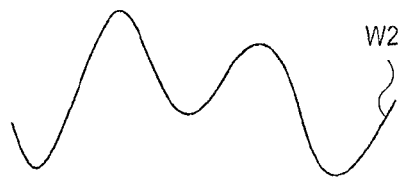
FIG. 3 is a schematically enlarged diagram of a pressure waveform in the cleaning liquid inside the pipes when bubbles are not present.
Figure 3:
Figure 4:
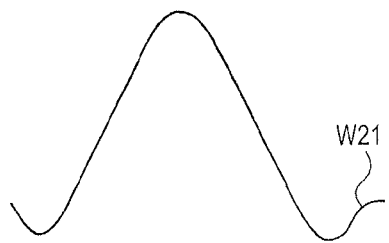
FIG. 4 is a schematically enlarged diagram of a pressure waveform in the cleaning liquid inside the pipes when many bubbles are present.
Figure 4:

Here, FIG. 3 is a schematically enlarged diagram of pressure waveform W2, and illustrates a case where bubbles are not present in the cleaning liquid Wa inside the pipes 15. In such a case, the pressure waveform forms two large heads. On the other hand, if bubbles are present in the cleaning liquid Wa, pressure is transmitted slowly due to the bubbles, resulting in a slow change in the pressure, and the pressure waveform W2 becomes pressure waveform W21 forming only one large head as shown in FIG. 4. The pressure waveform W21 shown in FIG. 4 is a waveform in a case where many bubbles are present in the cleaning liquid Wa, and as the amount of bubbles decreases, the waveform becomes more similar to the pressure waveform W2 shown in FIG. 3.

Figure 5:
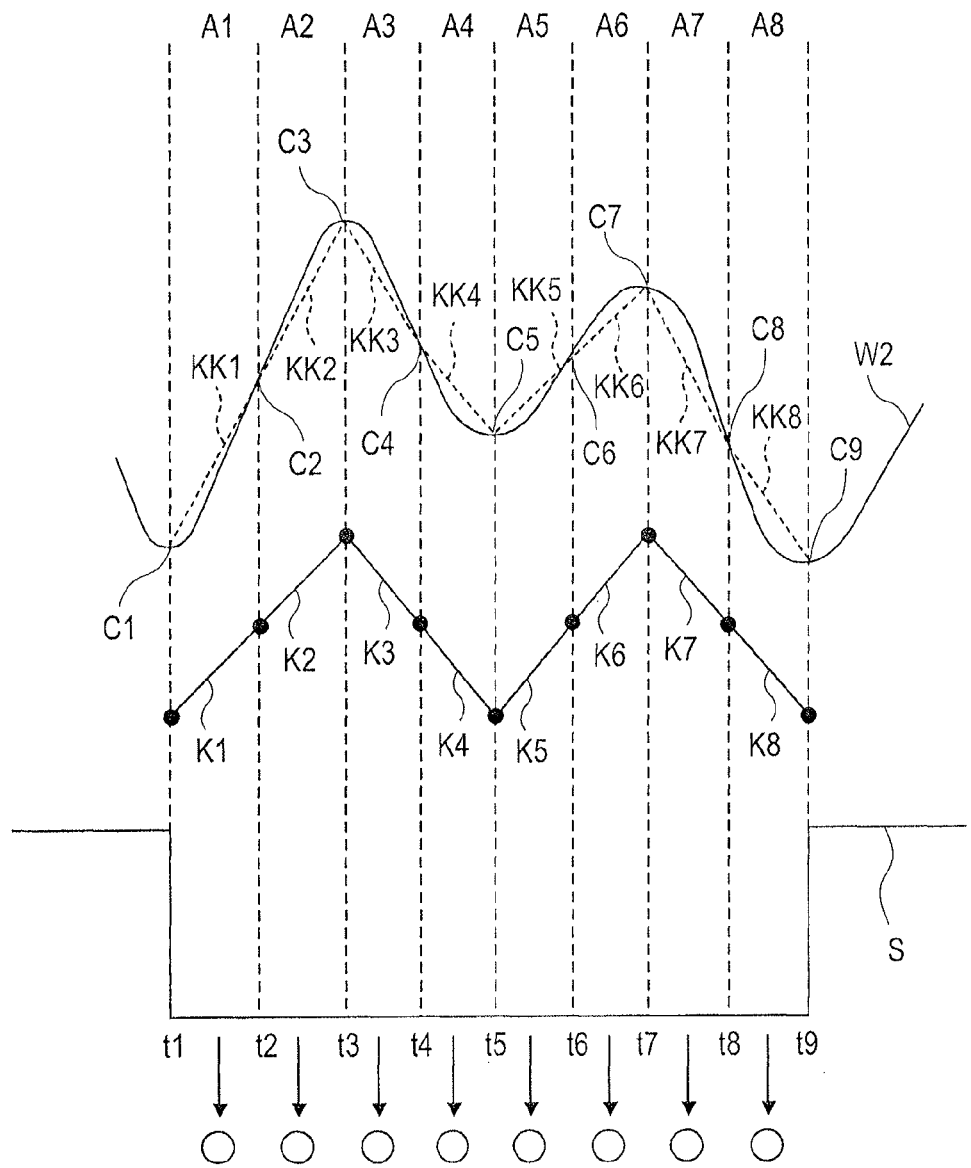
FIG. 5 is an explanatory diagram explaining a determining process when bubbles are not present in the cleaning liquid inside the pipes.

Thus, in the present embodiment, as shown in FIG. 5, the segment of the pressure waveform W2 is divided into a plurality of segments A1 to A8 along the time axis, and in the respective segments A1 to A8, reference slopes K1 to K8 of the pressure waveform W2 indicating the absence of bubbles and the slopes of the respective segments of the pressure waveform detected by the pressure sensor 16 are respectively compared. The number of segments in which the slopes of the respective segments exceed predetermined slope ranges from the respective reference slopes K1 to K8 are counted, and when the counted value is one or more, it is determined that bubbles are present inside the pipes 15.

Specifically, as shown in FIG. 5, segments A1 to A8 corresponding to the pressure waveform W2 indicating the absence of bubbles, which are obtained by dividing the waveform along predetermined sampling time points t1 to t9 are set, and reference slopes K1 to K8 for the respective segments A1 to A8 corresponding to the pressure waveform W2 indicating the absence of bubbles are set. The sampling time points t1 to t9 preferably correspond to a maximum point or minimum point of the pressure waveform W2, for example. The pressure signal obtained by the pressure sensor 16 is converted into digital pressure voltage value by the processing section 33a. The detecting section 33b detects pressure voltage values C1 to C9 of the respective sampling time points t1 to t9. The calculating section 33c calculates slopes KK1 to KK8 of the respective segments A1 to A8. For example, slope KK1 for the segment A1 is calculated by the formula:

$$KK1=(C2-C1)/(t2-t1).$$

The determining section 33d subtracts the respective reference slopes K1 to K8 from the respective slopes KK1 to KK8, and when the subtraction result is within a predetermined absolute value range, determines "○" and when the subtraction result is out of the predetermined absolute value range, determines "X." When there is one or more "X" determinations, the determining section 33d determines that bubbles are present inside the pipes 15. For example, in FIG.

Figure 6:
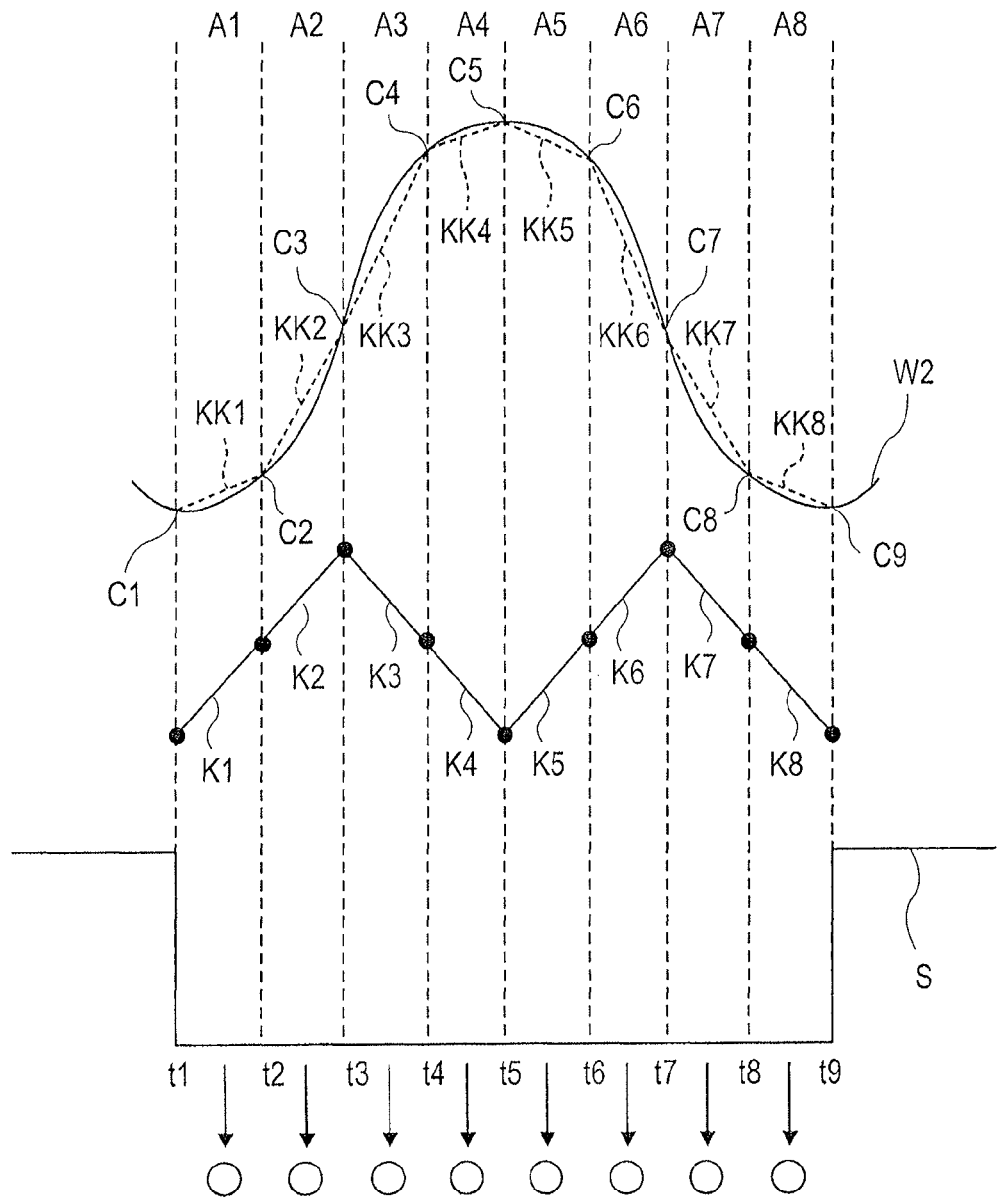
FIG. 6 is an explanatory diagram explaining a determining process when many bubbles are present in the cleaning liquid inside the pipes.

5, the determining section 33d determines "○" for all segments A1 to A8, and determines and outputs that bubbles are not present inside the pipes 15. On the other hand, in FIG. 6, the determining section 33d determines "X" for the segments A3 to A6. Since there are one or more "X" determinations, the determining section 33d determines and outputs that bubbles are present inside the pipes 15.

Figure 7:
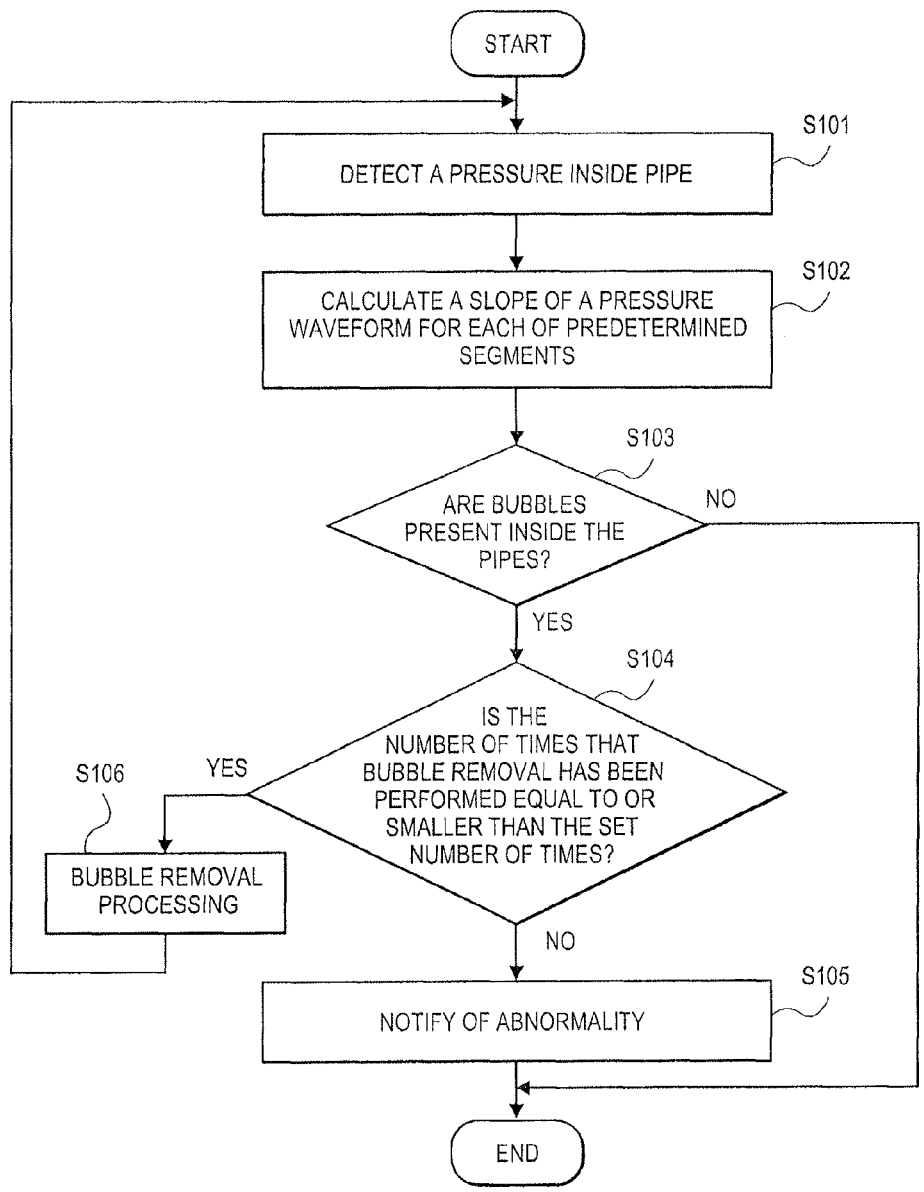
FIG. 7 is a flowchart illustrating a procedure of the processing to determine the presence or absence of bubbles inside the pipes by a bubble determining section.

Here, referring to the flowchart shown in FIG. 7, the procedure of processing to determine the presence or absence of bubbles inside the pipes 15 by the bubble determining section 33 will be explained. In FIG. 7, first, to check before beginning dispensing at the time of starting up an analyzing apparatus, under the control by the controlling section 31, the dispensing apparatus 1 drives the dispensing pump 13 to discharge the cleaning liquid Wa from the dispensing nozzle 11 after the cleaning inside thereof to the cleaning container 42 at the position P3. The processing section 33a converts the pressure waveform then detected by the pressure sensor 16 into a digital signal. Based on this converted digital signal, the detecting section 33b detects pressure waveform (step S101).

Thereafter, the calculating section 33c calculates slopes of the respective segments A1 to A8 based on the pressure waveform detected by the detecting section 33b (step S102). Thereafter, the determining section 33d compares the slopes KK1 to KK8 respectively calculated for the segments A1 to A8 and pre-established reference slopes K1 to K8 indicating the absence of bubbles, and determines the presence or absence of bubbles inside the pipes 15 based on the number of segments in which the slopes KK1 to KK8 are out of the predetermined slope ranges from the pre-established reference slopes K1 to K8 (step S103). Specifically, when the number of segments in which the slopes are out of the predetermined slope ranges is one or more, it is determined that bubbles are present inside the pipes 15. If it is determined that bubbles are not present (step S103: No), this processing is terminated. In this case, the determining section 33d may output a display that there are no bubbles inside the pipes 15, or the like, to the output section 35 via the controlling section 31. As a result of terminating this determining procedure, the dispensing apparatus 1 starts dispensing a liquid sample containing a specimen or a reagent.

On the other hand, if it is determined that bubbles are present (step S103: Yes), the determining section 33d judges whether or not the number of times that bubble removal has been performed is equal to or smaller than a set number of times (step S104). If the number of times that bubble removal has been performed is over the set number of times (step S104: No), such a case is a case in which bubbles have mixed inside the pipes 15 in spite of the bubble removal operation. Thus, the procedure moves to step S105, and the determining section 33d notifies of an abnormality (step S105), and outputs a display that there are bubbles inside the pipes 15, or the like, to the output section 35 via the controlling section 31.

Meanwhile, if the number of times that bubble removal has been performed is equal to or smaller than the set number of times (step S104: Yes), bubble removal processing is performed (step S106). This bubble removal processing is performed by outputting a controlling signal to the electromagnetic valve 17 to open the valve, and driving the cleaning liquid pump 18 to supply the cleaning liquid Wa in the cleaning liquid tank 19 to inside of the pipes 15. By this bubble removal processing, bubbles mixed inside the pipes 15 are discharged to the cleaning container 42 together with the cleaning liquid Wa. Thereafter, the determining section 33d returns to step S101, and repeats the processing of determining the presence or absence of bubbles inside the pipes 15 as described above.

In the present embodiment, since the pressure inside the pipes 15 can be detected by the pressure sensor 16, the presence or absence of bubbles inside the pipes 15 can be readily determined before dispensing. As a result, it is possible to reduce the time for carrying out reexamination or the like due to dispensing with low dispensing accuracy, thereby achieving reduced analysis time.

In a case of restarting dispensing after maintenance of the dispensing apparatus or after stopping the dispensing operation for a long time, bubbles may occur inside the pipes due to environmental temperature, air pressure, slight leakage or the like. Thus, it is also preferred to carry out the processing of determining the presence or absence of bubbles in accordance with the present embodiment in such a case.

In the aforementioned embodiment, it is determined that bubbles are present inside the pipes 15 when there are one or more "X" determinations. However, without limiting to this embodiment, the number of "X" determinations may be varied depending on small or large of difference between the pressure waveform indicating the presence of bubbles and the pressure waveform indicating the absence of bubbles.

Furthermore, although in the aforementioned embodiment predetermined slope ranges are set for determining "○" or "X," determination may be made depending on whether the slopes of the respective segments A1 to A8 are positive or negative, instead of using the slope ranges. For example, in a case in which reference slope K1 for the segment A1 is defined "positive," when the slope KK1 is "positive," "○" determination is made, and when the slope KK1 is "negative," "X" determination is made. This simplifies the determining processing by the determining section 33d.

Moreover, although in the aforementioned embodiment the segments A1 to A8 have the same time duration, without limiting to such an embodiment, time duration of the respective segments A1 to A8 may be varied in accordance with the pressure waveform indicating the absence of bubbles.

Furthermore, although in the aforementioned embodiment the presence or absence of bubbles is determined based on the pressure waveform W2 at the time of discharging the cleaning liquid Wa, without limiting to such an embodiment, the presence or absence of bubbles may be determined based on another pressure waveform occurring in the pipes 15.

INDUSTRIAL APPLICABILITY

As described above, the bubble presence/absence determining method and the dispensing apparatus of the present invention are useful for surely detecting the presence of bubbles before dispensing.

The invention claimed is:

1. A method of determining the presence or absence of bubbles within a pipe in a dispensing apparatus for performing a dispense, comprising the steps of:
   a) detecting pressure within the pipe, before performing the dispense; and
   b) determining the presence or absence of bubbles within the pipe based on the detection result of the pressure within the pipe,
   wherein step b) includes:
   calculating a slope of each of a plurality of pressure waveform portions obtained by dividing a waveform of the detected pressure such that the plurality of pressure waveform portions correspond to a plurality of segments along the time axis;
   determining whether or not the calculated slope of each of the plurality of pressure waveform portions is outside a predetermined range; and determining the presence or absence of bubbles within the pipe, based on the number of segments in which the respective calculated slopes of the plurality of pressure waveform portions are determined to be outside the predetermined range.

2. The method according to claim 1, wherein, in step b), it is determined that bubbles exist within the pipe when the number of segments in which the respective calculated slopes of the plurality of pressure waveform portions are determined to be outside the predetermined range is one or more.

3. A dispensing apparatus for performing a dispense, comprising:

a detecting means for detecting pressure within a pipe before performing the dispense; and a determining means for determining the presence or absence of bubbles within the pipe based on the detection result of the pressure within the pipe, wherein the determining means includes:

means for calculating a slope of each of a plurality of pressure waveform portions obtained by dividing a waveform of the detected pressure such that the plurality of pressure waveform portions correspond to a plurality of segments along the time axis;

means for determining whether or not the calculated slope of each of the plurality of pressure waveform portions is outside a predetermined range; and means for determining the presence or absence of bubbles within the pipe, based on the number of segments in which the respective calculated slopes of the plurality of pressure waveform portions are determined to be outside the predetermined range.

4. The dispensing apparatus according to claim 3, wherein the determining means determines that bubbles exist within the pipe when the number of segments in which the respective calculated slopes of the plurality of pressure waveform portions are determined to be outside the predetermined range is one or more.

* * * * *